United States Patent [19]

Say

[11] Patent Number: 5,134,994

[45] Date of Patent: Aug. 4, 1992

[54] FIELD ASPIRATOR IN A SOFT PACK WITH EXTERNALLY MOUNTED CONTAINER

[76] Inventor: Sam L. Say, 1210 El Vago St., La Canada, Calif. 91011

[21] Appl. No.: 478,671

[22] Filed: Feb. 12, 1990

[51] Int. Cl.$^5$ .......................................... A61M 15/00
[52] U.S. Cl. ............................ 128/200.24; 128/205.12
[58] Field of Search .............................. 604/35, 319; 128/200.24, 205.12, 205.19, 206.22

[56] References Cited

U.S. PATENT DOCUMENTS

| | | | |
|---|---|---|---|
| D. 245,372 | 8/1977 | Kurtz et al. | D24/59 |
| D. 250,207 | 11/1978 | Kurtz et al. | D24/59 |
| D. 262,657 | 1/1982 | Ekbladh | D24/58 |
| D. 268,305 | 3/1983 | Stark | D3/71 |
| D. 270,948 | 10/1988 | Say | D24/59 |
| D. 281,120 | 10/1985 | Rabinowitz | D3/42 |
| D. 305,798 | 1/1990 | Say | D24/51 |
| 2,784,717 | 3/1957 | Thompson | 604/319 |
| 3,363,626 | 1/1968 | Bidwell et al. | 604/151 |
| 3,782,384 | 1/1974 | Timmermans | 604/321 |
| 3,915,189 | 10/1975 | Holbrook et al. | 137/205 |
| 3,989,046 | 11/1976 | Pannier, Jr. et al. | 604/319 |
| 4,275,731 | 6/1981 | Nichols | 604/319 |
| 4,545,414 | 10/1985 | Baum | 150/52 J |
| 4,798,580 | 1/1989 | De Meo et al. | 604/35 |
| 4,930,997 | 6/1990 | Bennett | 604/319 |

Primary Examiner—Edgar S. Burr
Assistant Examiner—Aaron J. Lewis
Attorney, Agent, or Firm—Christie, Parker & Hale

[57] ABSTRACT

A portable suction device for removing fluids blocking aspiration of a patient is disclosed. The device has a housing formed of a soft, but durable, material, a vacuum pump for generating suction, a battery pack for powering the pump, and a fluid container. A tube communicates the pump with the container to evacuate it, and another tube connects the evacuated container with the fluids blocking aspiration of the patient. The housing has a container support integrally attached thereto for supporting the container outside of the housing. The means for supporting is a non-rigid material like that of the housing, and has a closed cell material disposed in the non-rigid material for absorbing shocks to the container.

35 Claims, 9 Drawing Sheets

FIELD ASPIRATOR IN A SOFT PACK WITH EXTERNALLY MOUNTED CONTAINER

BACKGROUND OF THE INVENTION

The present invention relates to a portable aspirator, and in particular, to an aspirator having a suction pump and a container or canister for storing collected fluid.

In recent years, portable aspirators have gained popularity, in part due to increased awareness of the need for sanitary aspiration techniques to avoid the spread of disease. These aspirators are often used by fire fighters, paramedics, and other rescue and health workers. Desirable characteristics for a portable aspirator are that it be lightweight and easy to carry. Such aspirators must also be shock proof, especially when used by fire fighters and paramedics where it is very likely to be continually jostled. It is further desirable that the canister in which fluid from the patient is collected be quickly and easily replaceable, so that multiple patients can be handled in rapid succession. While many pre-hospital users will remove, empty and replace the canister, it is best to discard and replace the canister after each use, otherwise sanitary conditions are jeopardized. In any event, it has been difficult to achieve an aspirator device with a canister holder that is shock proof, yet enables the canister to be quickly and easily removed and replaced.

SUMMARY OF THE INVENTION

The present invention is a portable aspirator having a soft pack housing with a shock resistant externally mounted container support. In one embodiment, the aspirator has a housing of a soft, but durable, material, such as nylon. A vacuum pump for generating suction and a battery pack for powering the pump are disposed in the housing. An on/off switch for the device, and a regulator to regulate the suction force, are mounted to the outside of the housing for quick and easy operation. The soft pack housing has a container support also made of a soft, but durable, material and fixed to the housing. The support has a closed cell foam material snugly fitted in it for providing a shook resistant seat for a removable container. The vacuum pump is connected to the container to evacuate it. A tube having a suction tip also communicates with the interior of the container to provide suction force to drain fluid from a patient.

The interior of the housing is quickly and easily accessible, as the nylon material is provided with a zippered flap. The battery pack is mounted in a U-shaped slotted support and is electrically connected, using snapfit connectors for quick and easy replacement.

BRIEF DESCRIPTION OF THE DRAWINGS

The above features and advantages as well as additional features and advantages of the invention will be more evident upon reading the detailed description in conjunction with the drawings, in which.

DETAILED DESCRIPTION

The invention is an aspirator having a soft pack material housing with a shock absorbent externally mounted support for a container.

Figure 1:
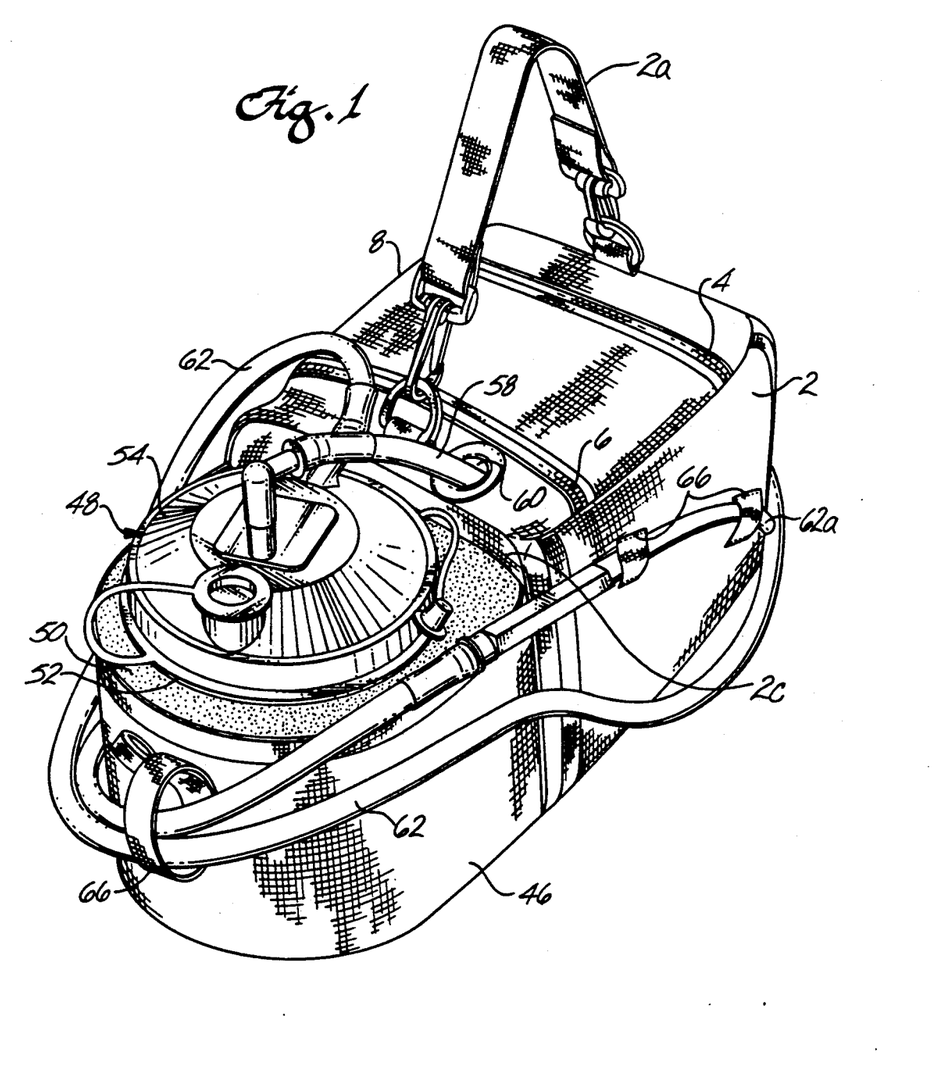
FIG. 1 is a perspective view of a portable aspirator with a container support attached to the outside of the aspirator's housing, in accordance with the invention.
Figure 2:
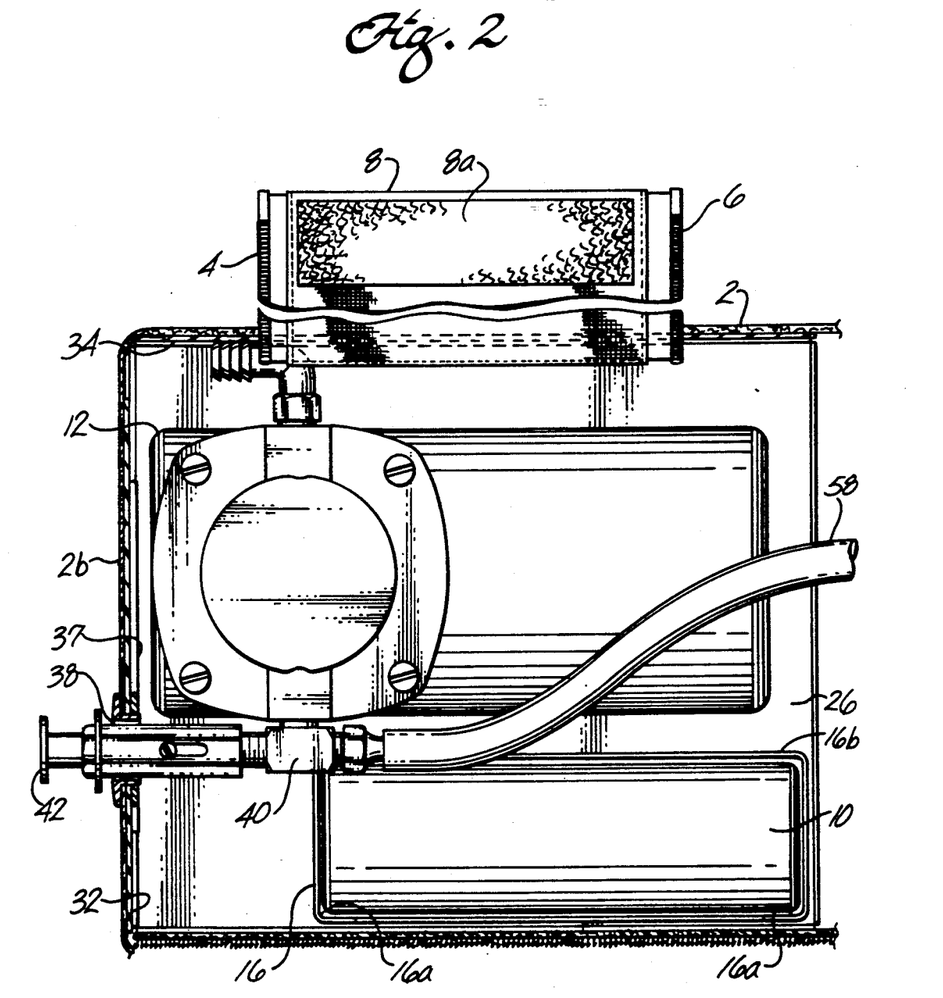
FIG. 2 is a top view of the inside of the device, without showing wires therein.

FIG. 1 is a perspective view of the exterior of the device, and FIG. 2 is a top view of the device, with the exterior partially removed to show components inside the device. The aspirator according to the invention has a housing 2 made of a soft, but durable, material such as a fabric, e.g., nylon. Other non-rigid but strong and durable materials may be used. A strap 2a is attached to the top of the housing so that one can carry the device over the shoulder. Housing 2 has a rectangular flap 8 that is permanently attached to housing 2 at one end of the flap and releasably attached to the housing at the other end. The housing has two parallel zippers 4,6 which run about half way around the housing and thus define the sides of flap 8 (shown closed in FIG. 1 and folded back in FIG. 2). Flap 8 opens for access to the inside of the housing. To releasably close flap 8, there is a velcro (RM) strip 8a (FIG. 2) on the inside of flap 8 and another such strip 8b (see bottom view of FIG. 9) on a corresponding portion of the housing. This construction allows the housing to be quickly opened and closed without the need for a third zipper or sharp turns in the path of zippers 4,6. The housing encloses a battery pack 10 and suction generator 12 (vacuum pump). Battery pack 10 is supported in the housing by a rigid U-shaped battery holder 16 with slots 16a and a side wall 16b to separate the battery pack from pump 12. The slotted U-shaped holder 16 enables the battery pack to be quickly and easily slid into and out of the holder.

Figure 3:
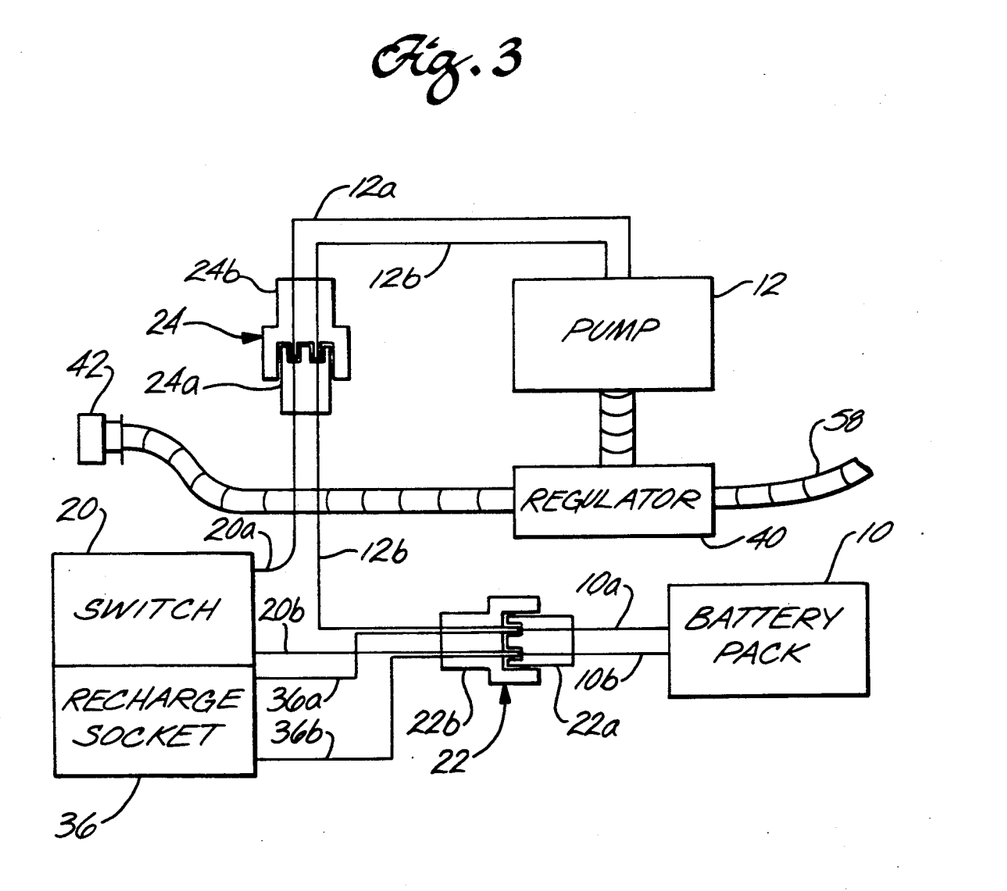
FIG. 3 is a schematic view of the components disposed inside the device, including the wires.
Figure 4:
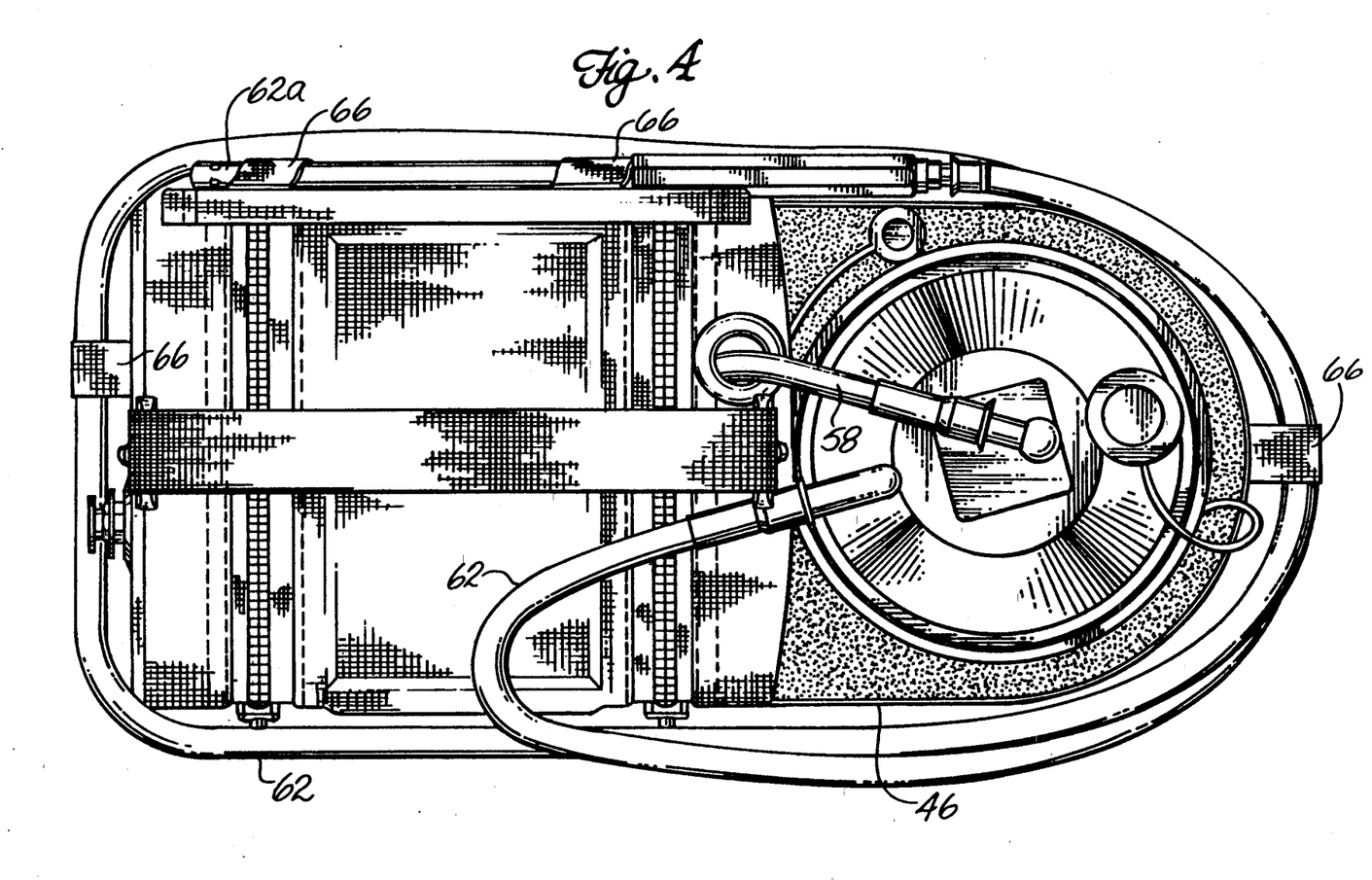
FIG. 4 is a top view of the device.
Figure 5:
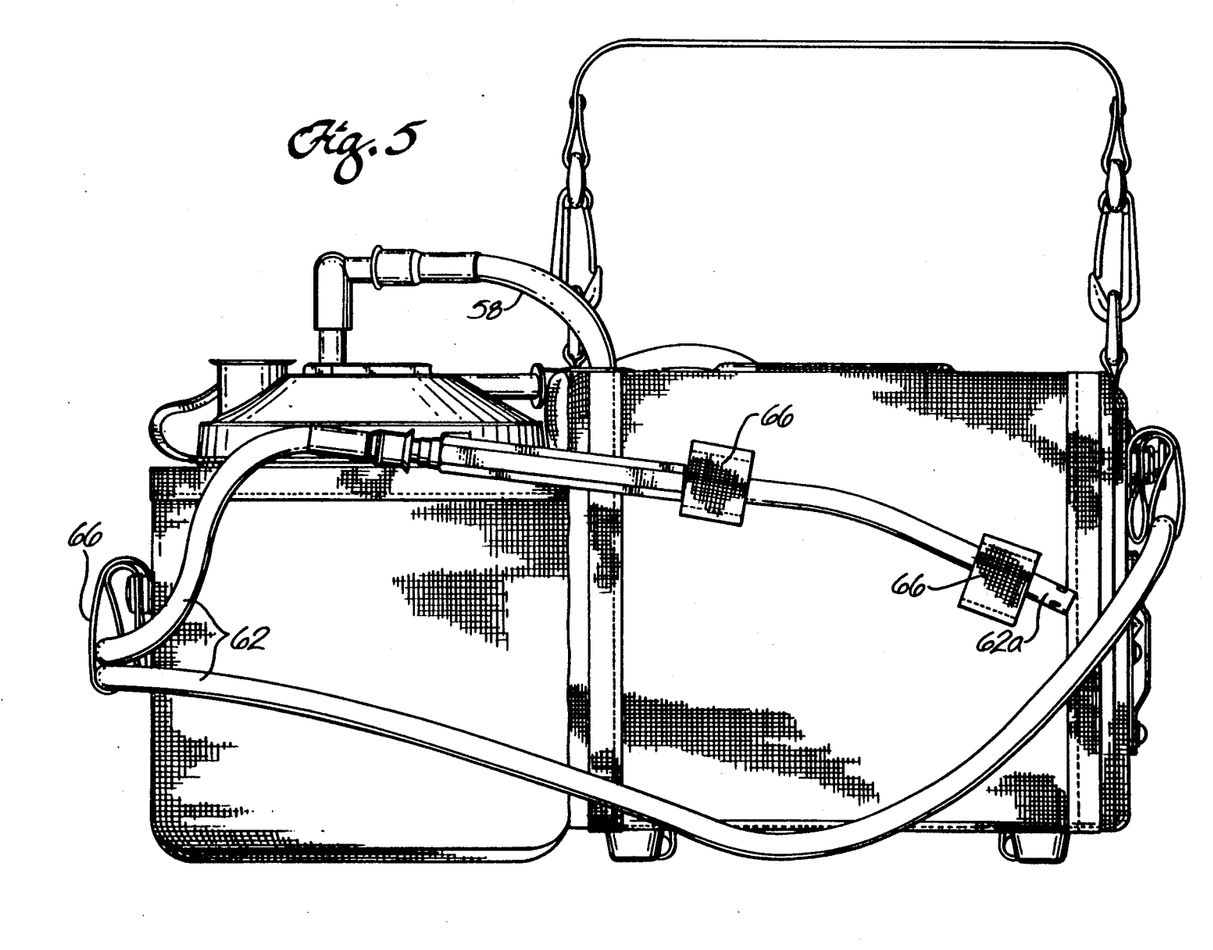
FIG. 5 is a first side view of the device.
Figure 6:
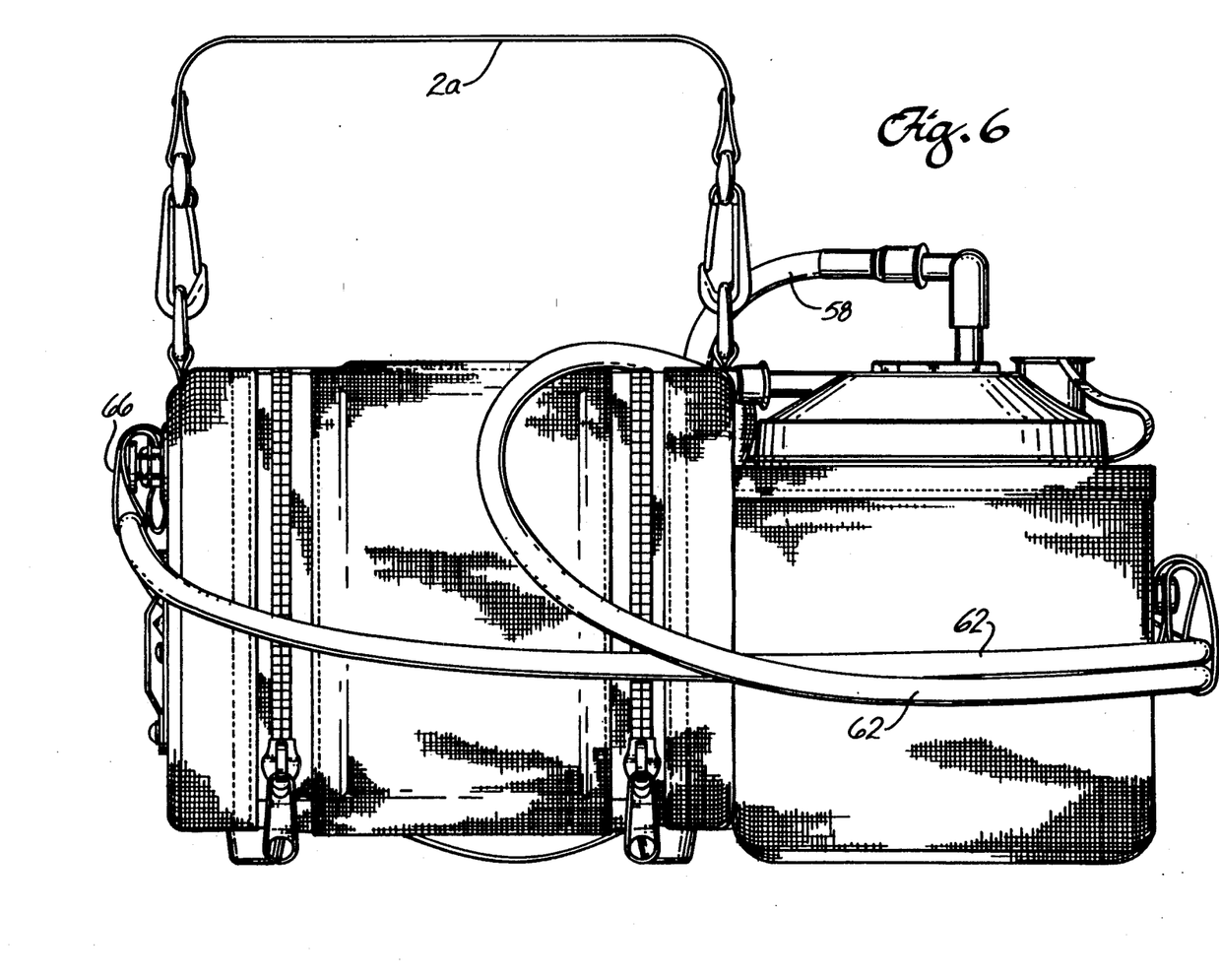
FIG. 6 is a second side view of the device.
Figure 7:
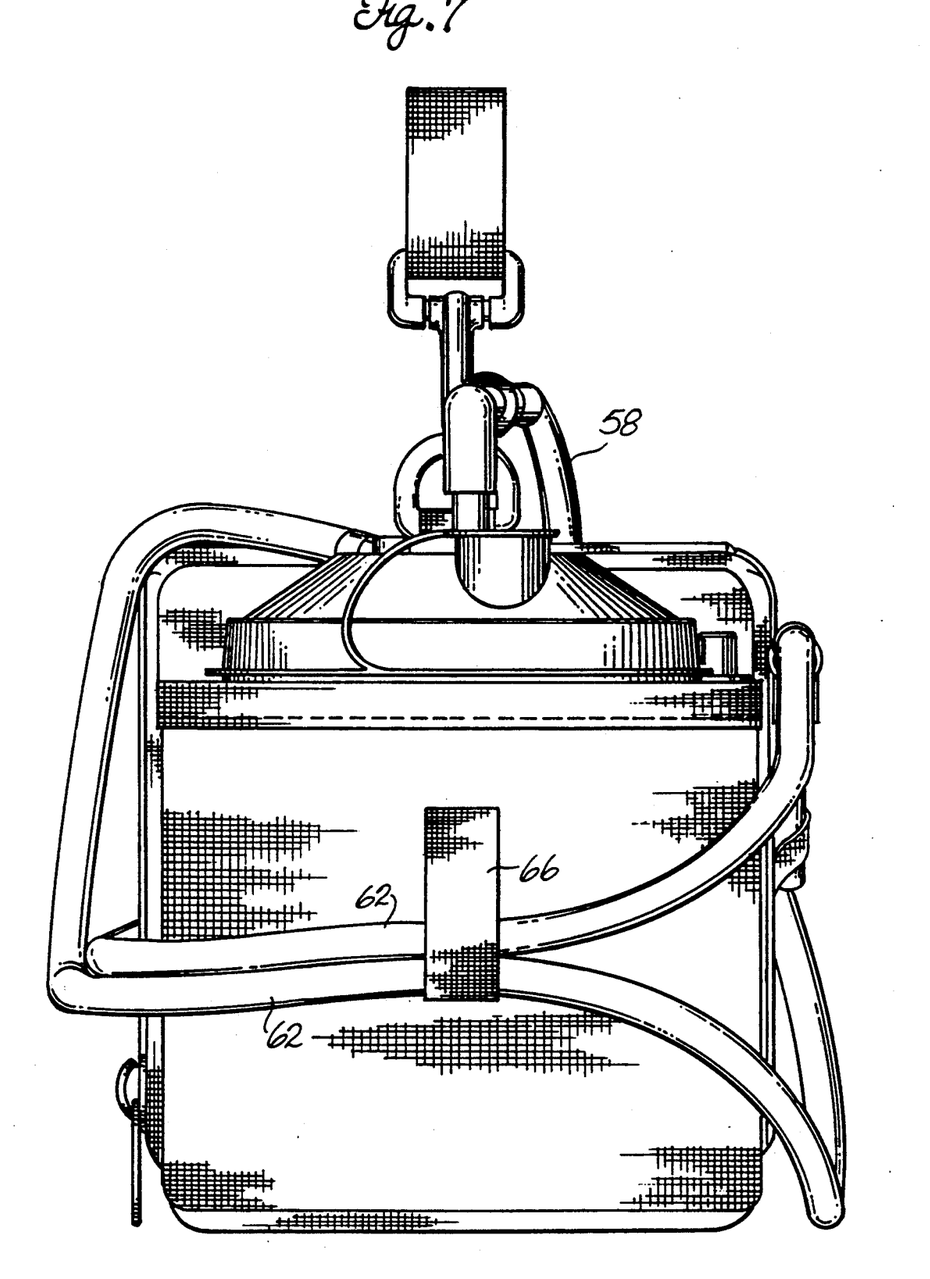
FIG. 7 is a front view of the device.

FIG. 3 is a schematic view of the working components of the device. Battery pack 10 is preferably rechargeable, such as a sealed lead acid battery or two Lifepack (RM) 5 batteries by Physio-Control, and connects to pump 12 and an on/off switch 20 using first and second snap-fit connectors 22, 24. These connectors 22, 24 each have male and female plastic connectors 22a, 24a and 22b, 24b, respectively, which allow the battery pack to be quickly and easily connected and disconnected.

Figure 9:
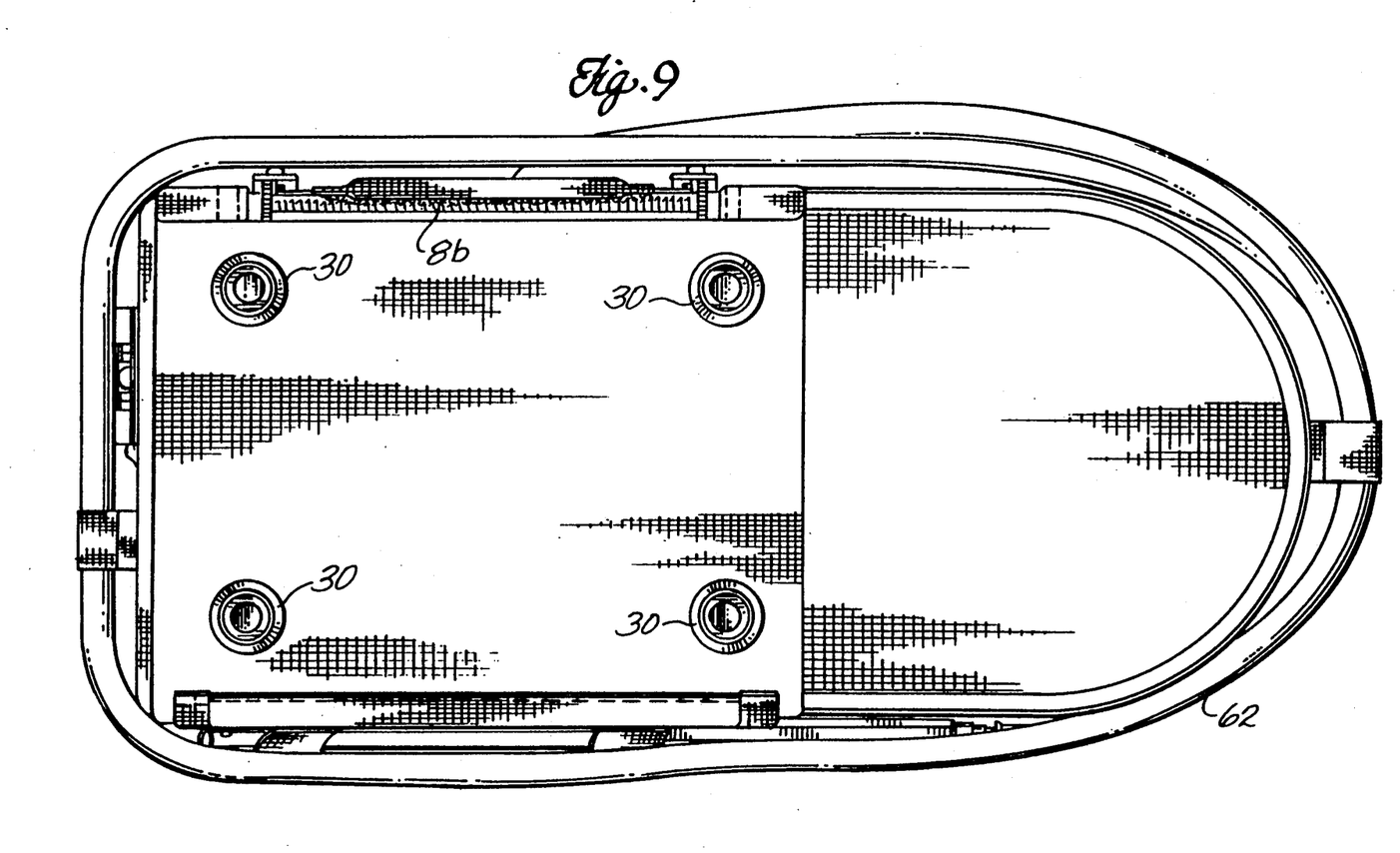
FIG. 9 is a bottom view of the device.

The housing has a rigid plate 26 (FIG. 2) positioned at its bottom to support battery holder 16 and pump 12. The holder and pump are both fixed to plate 26 by screws, bolts, or other suitable means. Plate 26 is in turn similarly secured through the housing to plastic or rubber feet 30 (FIG. 9).

Figure 8:
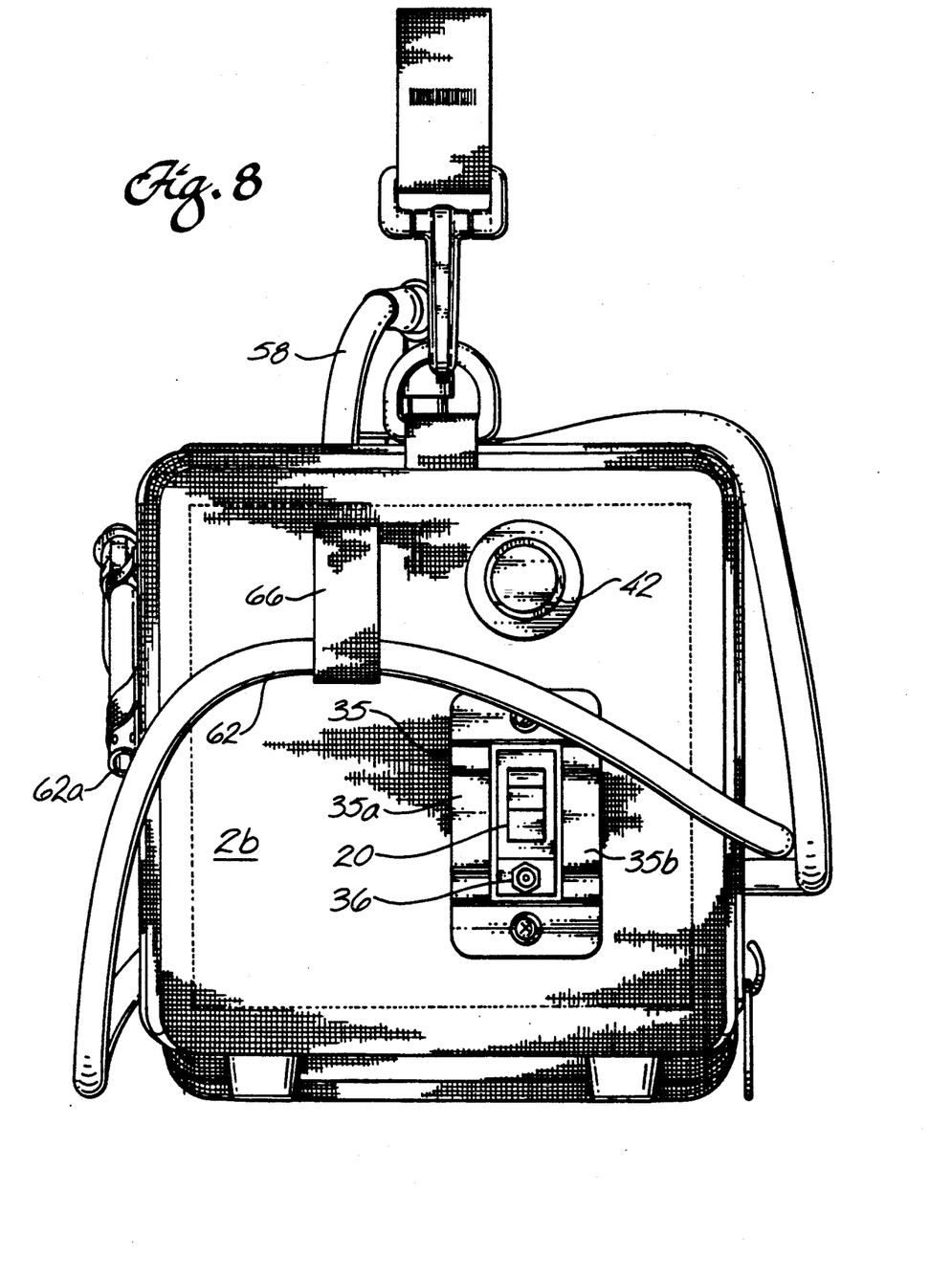
FIG. 8 is a rear view of the device.

Plastic liners 32, 34, preferably stitched to walls of housing 2, provide some rigidity to the housing. This is especially useful for rear wall 2b (FIG. 8), which has a plastic protective plate 35 secured through the wall to liner 34. Plate 35 surrounds on/off switch 20 and a recharge socket 36 connected to the battery pack, and has arms 35a, 35b (which extend out of the plane of the drawing toward the viewer) with respect to which the switch and socket are recessed, to prevent accidental triggering or deenergizing of the device. Another small and more rigid plate 37 mounts on the inside of liner 34, protective plate 35 being secured by suitable bolts (shown but unnumbered in FIG. 8) to the rigid plate 37. As best shown in FIG. 2, liner 34 and the rear wall also have an aperture 38 through which a regulator 40 connects to a switch 42. Regulator 40 is preferably a twoposition, vented regulator, preset to produce 80mm Hg (regulated pressure relative to sea level) at its low setting, which is for intubated patients or infants, and 550mm Hg or more at its high setting for other patients.

With renewed reference to FIG. 3, wiring between the pump, battery pack, switch and socket is shown. A circuit is formed between switch wire 20a, pump wire 12a, pump 12, pump wire 12b, battery pack wire 10a, battery pack 10, battery pack wire 10b, and switch wire 20b, for operating the device. A recharge circuit is formed by socket 36, socket wire 36a, wire 10a, battery pack 10, wire 10b, and socket wire 36b.

As best shown in FIG. 1, canister holder 46, also preferably of nylon, integrally attaches to front wall 2c of the housing. A canister 48, such as a plastic disposable canister (e.g. a catalogue #42-04-1-0 canister manufactured by Bemis Health Care) is supported in holder 46 and surrounded by a resilient, preferably closed cell foam layer 50 (e.g. ¾") snugly fitted into the holder. This protects the canister from jostling, while at the same time allowing a used canister to be quickly and easily replaced. (Preferably discarded and replaced, rather than emptied and replaced.) Moreover, this externally mounted holder keeps the canister, and thus all patient fluids, away from the wires, battery pack, pump and other working components of the device stored in the housing, for sanitary reasons as well as for protection of the working components. The closed cell foam confines any leaking patient fluids to the area where the canister is supported.

A bore 52 (FIG. 1) through the foam is shaped to fit and receive the canister 48. Preferably, the canister is tapered, and so is the foam. Top 54 of canister 48 has a first tube 58 in communication with it and regulator 40, via an aperture 60 in the front top of the housing. Accordingly, during operation of the device, the pump evacuates the canister.

With reference to FIGS. 4-7, which are top, first side, second (flap) side, and front views, respectively, a second tube 62 connects to the top of the canister. The second tube has a lot of slack, e.g. it is shown wrapped around the outside of housing 2, and has an open end 62a (suction tip) for insertion into a patient's mouth. Straps 66, some with snaps and some without, hold the second tube 62 and suction tip 62a in place.

With the above construction, the suction device according to the invention has many advantages. The canister is outside of the housing for quick and easy replacement, and for minimizing the possibility that leakage of fluid from the container can damage or contaminate the working components of the device. In addition, any such leakage is easy to clean up with the canister mounted outside the housing. The canister is supported and protected by the foam layer to minimize the effect of any mechanical shock, which is quite likely when the device is used by fire fighters, paramedics, or the like. The non-rigid housing and container holder minimize the effect of shock on the device as a whole, while the bottom support plate supplies a rigid surface on which to mount the battery pack holder and pump. The zipper and velcro (RM) flap, together with the slotted U-shaped battery pack holder and the snap connectors enable quick and easy replacement of the battery pack.

The controls, i.e., the on/off switch, recharge socket and regulator switch are mounted on the outside of the housing for quick and easy access, and the on/off switch is protected from accidental engagement or disengagement.

The regulator has two positions preset at appropriate low and high settings for quickly setting the appropriate pressure depending on the patient. The tubing and its suction tip for insertion into the patient are located outside of the housing for quick and easy access.

The above described embodiment of the invention is one example of the device, and is not intended to limit the scope of the claims, as there will be many variations of the disclosed embodiment which will be covered by the claims. For example, instead of a zippered flap with velcro (RM), a flap with snaps and velcro (RM), or just snaps, is suitable.

What is claimed is:

1. A portable suction device comprising:
    a housing made from a non-rigid material;
    means for generating suction disposed in the housing;
    a container;
    means for applying the suction to suck fluid into the container; and
    means fixed to the housing for supporting the container outside of the housing, the means for supporting being made from a non-rigid material and including a resilient shell for absorbing shocks to the container, and the container being disposed in the resilient shell.

2. The device of claim 1 wherein the resilient shell comprises a closed cell material.

3. The device of claim 1 wherein the means for supporting comprises the same non-rigid material as the housing and is integrally attached to the housing.

4. The device of claim 1 wherein the means for generating suction comprises a vacuum pump and a battery pack for powering the vacuum pump.

5. The device of claim 1 wherein the means for applying suction comprises a first conduit connected to the means for generating and to the container to evacuate the container, and a second conduit for connection between the container and the fluid to be sucked.

6. The device of claim 1 wherein the closed cell material has an open portion for insertion and removal of the container.

7. The device of claim 1 wherein the suction device has an on/off switch, the housing has an opening formed therein, and the on/off switch is mounted proximate the opening so as to be accessible from outside of the housing.

8. The device of claim 1 wherein the housing has a plurality of zippers for opening and closing the housing.

9. The device of claim 1, wherein the housing has a strap for carrying the device.

10. The device of claim 5 wherein the housing has means for releasably holding the second conduit.

11. The device of claim 5, further comprising means for supporting the second conduit outside the housing.

12. The device of claim 4 further comprising a U-shaped slotted holder in which the battery pack is slidably fitted.

13. The device of claim 12 further comprising an on/off switch for the vacuum pump, and means for providing snap-fit electrical connections between the battery pack, vacuum pump, and on/off switch.

14. A portable suction device for removing fluids blocking aspiration of the patient, the device comprising:
    a housing;
    means for generating suction disposed in the housing;

a container;

means for applying the suction to the container to evacuate it;

means for connecting the evacuated container with the fluids blocking aspiration of the patient; and means fixed to the housing for supporting the container outside of the housing, the housing comprising a first non-rigid material and the means for supporting comprising a second non-rigid material integrally attached to the housing and a resilient shell disposed in the second non-rigid material for absorbing shocks to the container, the container being disposed in the resilient shell.

15. The device of claim 14 wherein the resilient shell comprises a closed cell material.

16. The device of claim 14 wherein the first and second non-rigid materials are the same.

17. The device of claim 14 wherein the means for generating suction comprises a vacuum pump and a battery pack.

18. The device of claim 14 wherein the means for applying suction comprises a first conduit connected to the means for generating and to the container, and a second conduit for connection between the container and the fluid to be sucked.

19. The device of claim 14 wherein the closed cell material has an open portion for insertion and removal of the container.

20. The device of claim 14 wherein the suction device has an on/off switch mounted to the outside of the housing, the housing having an opening formed therein for connection of the switch to the means for generating.

21. The device of claim 20 further comprising means for protecting the on/off switch from accidental engagement and disengagement.

22. The device of claim 17 further comprising a U-shaped slotted holder in which the battery pack is slidably fitted.

23. The device of claim 22 further comprising an on/off switch for the vacuum pump, and means for providing snap-fit electrical connections between the battery pack, vacuum pump, and on/off switch.

24. The device of claim 1 wherein the closed cell material has an open portion for insertion and removal of the container.

25. The device of claim 7 further comprising a regulator for the means for generating suction, the regulator being operable from outside the housing.

26. The device of claim 20 further comprising a regulator for the means for generating suction, the regulator being operable from outside the housing.

27. The device of claim 1, further comprising a regulator having at least two preset positions for the means for generating suction.

28. The device of claim 14, further comprising a regulator having at least two preset positions for the means for generating suction.

29. The device of claim 18, further comprising means for supporting the second conduit outside the housing.

30. The device of claim 7 further comprising means for protecting the on/off switch from accidental engagement and disengagement.

31. The device of claim 4 further comprising a rigid plate disposed in the housing and having a top surface for supporting the vacuum pump, and a U-shaped holder mounted on the top surface of the rigid plate for slidably receiving the battery pack.

32. The device of claim 31 further comprising feet for the housing mounted on a bottom surface of the rigid plate.

33. The device of claim 17 further comprising a rigid plate disposed in the housing and having a top surface for supporting the vacuum pump, and a U-shaped holder mounted on the top surface of the rigid plate for slidably receiving the battery pack.

34. The device of claim 33 further comprising feet for the housing mounted on a bottom surface of the rigid plate.

35. The device of claim 14 wherein the container is frangible.

* * * * *